United States Patent [19]

Barton

[11] Patent Number: 5,514,794

[45] Date of Patent: May 7, 1996

[54] ANTIBODY-DRUG CONJUGATES

[75] Inventor: Russell L. Barton, Indianapolis, Ind.

[73] Assignee: Eli Lilly and Company, Indianapolis, Ind.

[21] Appl. No.: 644,366

[22] Filed: Jan. 22, 1991

Related U.S. Application Data

[62] Division of Ser. No. 269,815, Nov. 10, 1988, Pat. No. 5,010,176.

[51] Int. Cl.$^6$ .................................................. C07D 265/30
[52] U.S. Cl. ............................ 544/106; 560/41; 560/49; 560/17; 560/61; 560/139; 560/153; 560/154; 560/171; 546/51; 562/400
[58] Field of Search .......................... 540/478; 514/283; 560/49, 152, 181, 169, 19, 39, 139, 171, 153, 154, 41, 49, 17, 61; 546/51; 544/106

[56] References Cited

U.S. PATENT DOCUMENTS

| | | | |
|---|---|---|---|
| 3,905,871 | 9/1975 | Rubenstein et al. | 435/188 |
| 4,631,190 | 12/1986 | Shen et al. | 514/2 |
| 4,671,958 | 6/1987 | Rodwell et al. | 424/85.8 |
| 4,695,624 | 9/1987 | Marburg et al. | 530/395 |
| 4,762,915 | 8/1988 | Kung et al. | 530/405 |
| 4,764,368 | 8/1988 | Blattler et al. | 514/2 |

FOREIGN PATENT DOCUMENTS

| | | | |
|---|---|---|---|
| 243929 | 11/1987 | European Pat. Off. | 514/2 |
| 247792 | 12/1987 | European Pat. Off. | 540/478 |
| 253202 | 1/1988 | European Pat. Off. | 514/2 |
| 2137210 | 3/1983 | United Kingdom | 540/478 |
| 2181126 | 4/1987 | United Kingdom | 540/478 |

OTHER PUBLICATIONS

Grant and Hackh's Chemical Dictionary (McGraw–Hill New York, 1981) p. 196.
Plieninger, et al., Chemical Abstracts, vol. 74, 1971 Abstract 125317t.
Merck Index (Rahway, N.J. Merck and Co. 1989) pp. 540–541.
Szantay et al., Chemical Abstracts, vol. 106, 1987 Abstract 113543e.
Blair, et al. J. Immunological Methods, 59 (1983) 129–143.
Shen et al. Biochem and Biophys Res. Commun. 102(8), 1981 pp. 1048–1054.
Singh, et al. J. Hetercyclic Chem. 19, 1581 (1982).
King et al. Biochemistry, 1986 23, 5774–5779.
Ghose, Methods in Enzymology, 1983, New York, Academic Press, pp. 280 to 333.
Ghose et al. CRC Critical Reviews in Therapeutic Drug Carrier Systems, (CRC, (Boca Raton, Florida 1987) pp. 263 to 358.
Benjamin, et al. Immunology, a Short Course (New York, J.Wiley and Sons, 1991) pp. 263 to 266.
Lewin et al. Heterocycles vol. 14 (12) 1988 pp. 1915–1920.

*Primary Examiner*—Mukund J. Shah
*Assistant Examiner*—P. K. Sripada
*Attorney, Agent, or Firm*—Paul J. Gaylo; Joseph A. Jones

[57] ABSTRACT

Derivatized drugs are prepared with a linker consisting of a malonate, wherein the drug is linked through a methylene to the 2-position carbon of the malonate.

4 Claims, No Drawings

ANTIBODY-DRUG CONJUGATES

This Application is a Division of Ser. No. 07/269815 now U.S. Pat. No. 5,010,176 filed Nov. 10, 1988.

FIELD OF THE INVENTION

The present invention belongs to the fields of organic chemistry, pharmaceutical chemistry and immunology, and provides conjugates of antibodies with drugs. The conjugates are useful for the targeted administration of the drugs, wherein the antibody directs the drug to the tissue or cell where the drug is needed. Conjugation of the antibody and drug is achieved by means of a divalent linker which bonds to the antibody at one bonding point, and to the drug at the other. Intermediates for the preparation of the conjugates are also provided.

BACKGROUND OF THE INVENTION

The science of pharmaceutical chemistry has progressively provided more and more specific and potent drugs for the treatment and prevention of illness. However, until quite recently, there has been no means to direct a drug to the specific part of the body where it is needed. Thus, although it is often possible to treat a patient with a drug which has the specific effect which is needed, and no other effect on the body, it is still necessary to administer a whole-body dose. On the other hand, if it were possible to direct a drug to the organ, tissue or even cell in need of the treatment, it would often be possible to administer an extremely small total dose, since the drug would concentrate itself where it is needed. The advantage in safety to the patient and economy of drug is obvious.

For some years now, the science of immunology has been attempting to provide such targeted treatments, by conjugating drugs with antibodies which are directed to specific antigens associated with the locations where the drug is needed. Patents and scientific articles concerning such antibody-drug conjugates are now numerous. However, up to the present time, no antibody-drug conjugate is approved for therapeutic use.

SUMMARY OF THE INVENTION

The present invention provides a physiologic- ally-acceptable drug conjugate of the formula

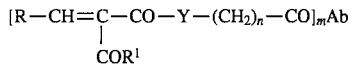

wherein
- Ab is an antibody or antigen-recognizing fragment thereof, which recognizes an antigen associated with a cell to which delivery of the drug is desirable;
- R is a drug having a reactively-available amino, hydroxy or thiol function;
- $R^1$ is a carboxylic acid protecting group;
- Y is —O—, —NH—, —NCH$_3$— or —NC$_2$H$_5$—;
- n is an integer from 1 to about 8;
- m is an integer from 1 to about 10.

The invention also provides pharmaceutical compositions comprising a conjugate of the invention and a parenterally-administrable medium, and treatment methods comprising the parenteral administration of a conjugate of the invention to a patient in need of treatment with the drug.

Also provided are intermediate malonates of the formula

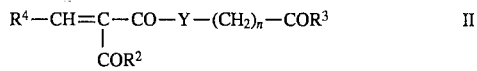

wherein
- $R^2$ is hydroxy, a carboxylic acid protecting group or a moiety which completes a salt of the carboxylic acid;
- $R^3$ is hydroxy, a carboxylic acid protecting group, a carboxylic acid activating group, or a moiety which completes a salt of the carboxylic acid;
- $R^4$ is $C_1$–$C_4$ alkoxy.

The invention further provides a modified antibody or antibody fragment of the formula

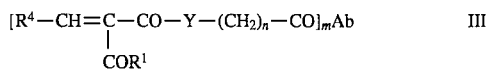

The invention also provides a derivatized drug of the formula

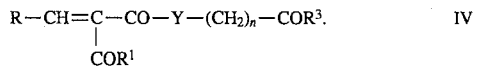

DETAILED DESCRIPTION OF THE INVENTION

Throughout the present document, all temperatures are in degrees Celsius. All expressions of percentage, concentration and the like are in weight units, unless otherwise stated. All references to concentrations and dosages of drug conjugates are in terms of the amount or concentration of the drug contained in the conjugate.

In the above general formulae, the term $C_1$–$C_4$ alkoxy refers to methoxy, ethoxy, propoxy, isopropoxy and the various isomeric butoxy groups including n-butoxy and t-butoxy.

Throughout the present document, the compounds will be referred to in general as malonates. It will be realized, however, that those compounds wherein Y is an amino function are properly called malonamates, and that term will be used where such compounds are specifically meant.

The term, carboxylic acid protecting group, refers to organic groups which are useful for the protection of carboxylic acids while reactions are carried out at other locations. Such groups are extremely widely used in synthetic chemistry, particularly in peptide chemistry, and protecting groups are well known to organic chemists. A particularly convenient textbook on the subject is Greene, Protective Groups in Organic Synthesis, John Wiley and Sons, New York, 1981. Acid protecting groups are discussed by Greene in Chapter 5. The most preferred protective groups in the context of the present invention are lower alkoxy groups, particularly ethoxy. Further preferred and convenient acid protecting groups include, as taught by Greene, for example, methoxymethoxy, tetrahydropyranyloxy, tetrahydrofuranyloxy, benzyloxymethoxy, phenacyloxy and substituted phenacyloxy, 2,2,2-trichloroethoxy and other haloethoxy's, trimethylsilylethoxy, methylthioethoxy, toluenesulfonylethoxy, t-butoxy, cyclopentoxy, benzyloxy, diphenyl- and triphenylmethoxy and the like, as well as amide-forming groups such as amino, ethylamino, dimethylamino, pyrrolidino, morpholino, piperidino, diethylaminoethylamino, morpholinoethylamino, benzylmethylaminoethylamino and the like.

The term, a carboxylic acid activating group, includes groups used in synthetic organic chemistry to increase the reactivity of a carboxylic acid. Such groups are frequently used by synthetic chemists, and include groups such as benzenesulfonyloxy, methanesulfonyloxy, toluenesulfonyloxy, phthalimidyloxy, succinimidyloxy, chloro, benzotriazolyloxy, bromo, azido and the like. The preferred activating groups in the present invention are N-succinimidyloxy, phthalimidyloxy and benzotriazolyloxy.

The term, a moiety which completes a salt of the carboxylic acid, refers to the commonly understood chemical moieties which, linked through an oxygen atom, form salts of carboxylic acids. For example, such salt-forming moieties as alkali metals, amine groups and quaternary ammonium groups are desirable. More particularly, sodium, potassium, lithium, $C_1$–$C_4$ alkylamino, dialkylamino and trialkylamino groups and quaternary ammonium groups wherein the nitrogen atom is substituted with four hydrogen, $C_1$–$C_4$ alkyl, phenyl or benzyl moieties are more preferred. For further example, quaternary ammonium groups such as ammonium, tetramethylammonium, diethyl-dimethylammonium, diethyl-dibutylammonium, benzyl-trimethylammonium, t-butyl-trimethylammonium, phenyl-triethylammonium, diethyl-dipropylammonium, s-butyltrimethylammonium, isobutyl-tri-ethylammonium and the like are useful and may be chosen for convenience in the circumstances. Further, such amines as methylamine, butylamine, triethylamine, dipropylamine, diethanolamine and the like are convenient for salt formation.

The drug conjugates of the present invention are composed of antibodies, drugs of certain chemical classes and organic chemical groups which link the antibodies and drugs. The invention also provides intermediate malonates used for the preparation of the conjugates, and modified antibodies prepared by reaction of antibodies, or antibody fragments, with the malonate intermediates in activated form. The antibodies and drugs will first be discussed individually, then the malonate intermediates and the synthesis will be explained, and, finally, examples of the synthesis and biological performance of the conjugates will be shown.

The Antibody

It will be understood that the function of the present drug conjugates is determined by the biological efficacy of the drug and the antigenic selectivity of the antibody. An antibody is chosen which will recognize an antigen associated with a cell to which the particular drug is beneficially delivered. For example, if the drug is an anti-neoplastic, then an antibody which recognizes an antigen associated with tumor cells would be chosen. If the drug is an antibacterial, for example, a cephalosporin, an antibody would be chosen which recognizes a bacterial antigen. Depending on the characteristics of the drug to be used, it may be preferred in a given case to choose an antibody which is internalized by the cell, or it may be preferred to use an antibody which remains on the cell surface by recognizing a surface antigen.

The source of the antibody is not critical to the present invention. It may be chosen from any class or subclass of immunoglobulin including IgG, IgA, IgM, IgE and IgD. Similarly, the species of origin is not critical so long as the antibody targets a cell where the effect of the drug is useful.

In the present state of the art, monoclonal antibodies are most used in drug conjugates, and use of them is preferred in the present invention. However, polyclonal antibodies are not excluded. A newer type of antibody is the chimeric antibody, which is prepared in the laboratory by recombinant technology which permits expression of a modified DNA which encodes the antigen-binding region of any desired antibody, and also encodes any other desired amino acid sequences. Thus, chimeric antibodies of which one portion is derived from one species, and another portion is derived from another species may be obtained and used in the present invention.

The origin and nature of the antibody is not otherwise critical, so long as it targets the cell to be treated and is not, in itself, toxic to the patient. Those of ordinary skill can readily prepare conjugates with a candidate antibody and evaluate them. Some discussion of the method of evaluating antibodies and conjugates will be provided for convenience. First, the antibody should be produced by a hybridoma which is sufficiently stable to allow preparation of reasonable quantities of antibody. The antibody itself should be amenable to purification, and in particular should be sufficiently water-soluble to allow chemical manipulations at reasonable concentration.

Conjugates prepared with the candidate antibody are first evaluated for antigen-binding capacity. A modest reduction from the binding capacity of the free antibody is expected and acceptable. Then, the conjugate is tested to determine its in vitro potency, such as cytotoxicity in the case of anti-cancer drugs, against antigen positive cells. An effective conjugate can have potency somewhat less than the free drug in the same assay, because of its ability to bring a high concentration of drug to the cell. A conjugate which is accepted in the first two tests is then evaluated in a nude mouse human tumor xenograft model, as taught by Johnson and Laguzza, *Cancer Res.* 47, 3118–22 (1987). The candidate conjugate should be tested in nude mice against the free drug, a mixture of free drug and free antibody, and a conjugate with a non-targeting immunoglobulin, and should exhibit improved potency or safety over all. Dose ranging studies should be carried out in the xenograft model.

Conjugates which are potent in the xenograft model are submitted to tests in animals which are known to express the antigen of interest in a pattern similar to that seen in humans. If the conjugate produces a significant degree of binding to the antigen in such tests, and if it is reasonably free of toxicity at doses predicted by the xenograft model to be therapeutic, the candidate conjugate can be considered to have therapeutic potential.

It will be understood that properly chosen fragments of antibodies have the same effect as the intact antibody. Thus, in the practice of this invention, fragments of antibodies, particularly F(ab')$_2$ fragments, which recognize an antigen associated with the cell to be treated, may be just as useful as are intact antibodies.

The exact mechanism by which the linker group reacts with and attaches to the antibody is not shown in Formula I, and is not perfectly known. The reaction presumably is an acylation, as is demonstrated below, and a number of locations on antibody molecules are subject to acylation. Most commonly, acylations of antibodies are thought to proceed on the free amino groups of lysine moieties. However, the acylation can also attack hydroxy groups, phenol groups, imidazole rings and perhaps other moieties.

Formula I indicates that from 1 to about 10 linker-drug moieties are attached to each molecule of antibody. Of course, the number of such moieties per antibody molecule is an average number because a given batch of conjugate will necessarily contain molecules having a range of ratios of drug-linker to antibody. The most efficient use of the expensive antibody is obtained, of course, when a number of molecules of drug are attached to each antibody molecule. However, the attachment of an excessive number of molecules of drug-linker moiety usually has an adverse effect on the antibody's ability to recognize and bind to its antigen, so a compromise value for m must be found. In general, the preferred value for m is from about 4 to about 10; another preferred value is from about 3 to about 8.

A great number of antibodies are available to immunologists for use in the present invention, and further useful antibodies are being disclosed in every issue of the relevant journals. It is impossible, and entirely unnecessary, to give an exhaustive listing of antibodies which can be applied in the practice of this invention. Immunologists and chemists of ordinary skill are entirely able to choose antibodies from sources such as the catalogue of the American Type Culture Collection, Rockville, Md., U.S.A., and Linscott's Directory of Immunological and Biological Reagents, published by Linscott's Directory, 40 Glen Drive, Mill Valley, Calif., U.S.A., 94941. Thus, it is a simple matter for the artisan in the field to choose an antibody against virtually any determinant, such as tumor, bacterial, fungal, viral, parasitic, mycoplasmal, or histocompatibility antigens, as well as pathogen surface antigens, toxins, enzymes, allergens and other types of antigens related to physiologically important cells.

The most preferred use of the present invention is in the delivery of cytotoxic drugs to cancer cells, particularly including squamous carcinoma cells, adenocarcinoma cells, small cell carcinoma cells, glyoma cells, melanoma cells, renal cell carcinoma cells, transitional cell carcinoma cells, sarcoma cells, cells of supporting tumor vasculature, and cells of lymphoid tumors such as leukemias and lymphomas. Appropriate antibodies for the targeting of all such cells are available, and sources can be located in Linscott. Alternatively, the necessary hybridomas for the production of such antibodies by conventional methods are obtainable through ATCC and other cell line collections.

A number of presently known antibodies are particularly interesting for use in the anticancer aspect of the present invention. A preferred specific antibody, for example, is L/1C2, produced by ATCC hybridoma HB9682.

Another interesting antibody is KS1/4, first disclosed by Varki et al., *Cancer Research* 44, 681–86 (1984). A number of plasmids which comprise the coding sequences of the different regions of monoclonal antibody KS1/4 are now on deposit and can be obtained from the Northern Regional Research Laboratory, Peoria, Ill., U.S.A. The plasmids can be used by those of ordinary skill to produce chimeric antibodies by recombinant means, which antibodies bind to a cell surface antigen found in high density on adenocarcinoma cells. The construction of such antibodies is discussed in detail in U.S. patent application Ser. No. 07/184,522, filed Apr.21, 1988. The following plasmids relate to KS1/4.

Plasmids pGKC2310, the coding sequence of the light chain, the signal peptide associated with the light chain, and the 5' and 3' untranslated regions; isolated from *E. coli* K12 MM294/pGKC2310, NRRL B-18356.

Plasmids pG2A52, the coding sequence of the heavy chain, the coding sequence of the signal peptide associated with the heavy chain, and the 5' and 3' untranslated regions; isolated from *E. coli* K12 MM294/pG2A52, NRRL B-18357.

Plasmid CHKC2-6, the coding sequence of the light chain variable region, the coding sequence of the signal peptide associated with the light chain, and a sequence encoding the light chain constant region of a human IgG; isolated from *E. coli* K12 DH5/CHKC2-6, NRRL B-18358.

Plasmid CHKC2-18, the coding sequence of a derivative light chain variable region, the coding sequence of the signal peptide associated with the light chain, and a sequence encoding the light chain constant region of a human IgG; isolated from *E. coli* K12 DH5/CHKC2-18, NRRL B-18359.

Plasmid CH2A5, the coding sequence of the heavy chain variable region, the coding sequence of the signal peptide associated with the heavy chain, and a sequence encoding the heavy chain constant region of human IgG1; isolated from *E. coli* K12 MM294/CH2A5, NRRL B-18360.

Plasmid CH2A5IG2, the coding sequence of the heavy chain variable region, the coding sequence of the signal peptide associated with the heavy chain, and a sequence which encodes the heavy chain constant region of human IgG2; isolated from *E. coli* K12 DH5/CH2A5IG2, NRRL B-18361.

Plasmid CH2A5IG3, the coding sequence of the heavy chain variable region, the coding sequence of the signal peptide associated with the heavy chain, and a sequence encoding the heavy chain constant region of human IgG3; isolated from *E. coli* K12 DH5/CH2A5IG3, NRRL B-18362.

Plasmid CH2A5IG4, the coding sequence of the heavy chain variable region, the coding sequence of the signal peptide associated with the heavy chain, and a sequence encoding the heavy chain constant region of human IgG4; isolated from *E. coli* K12 DH5/CH2AIG4, NRRL B-18363.

Antibody 5E9C11, produced by an ATCC hybridoma, HB21, recognizes transferrin receptor, which is expressed by many tumors. An antibody called B72.3, available from the National Cancer Institute, recognizes antigens expressed by both breast and colon carcinoma.

Two interesting antibodies with reactivities against non-tumor antigens are OKT3 and OKT4, which bind to peripheral T-cells and human T-helper cells, respectively. They are produced by hybridomas on deposit in the ATCC as CRL8001 and CRL8002, respectively.

Additional sources of antibodies useful for various therapeutic purposes are the following. Antihuman lymphocyte and monocyte antibodies, useful for immune modulation and tumor therapy, are produced by ATCC cultures HB2, HB22, HB44, HB78 and HB136. An antitransferrin receptor antibody, useful for tumor therapy, is produced by ATCC culture HB84. ATCC culture HB8059 produces an antibody against colorectal carcinoma monosialoganglioside, and culture HB8136 produces an antibody against mature human T-cell surface antigen, useful for immune modulation and T-cell leukemia therapy.

Still further, ATCC hybridoma HB9620 will produce a convenient anti-carcinoembyronic antigen called CEM231.6.7.

An immunologist or one knowledgeable in the drug targeting art, with the assistance of the commonly known publications in the field and the above guiding examples and description, can readily choose an antibody for the targeting of any appropriate drug to any desired cell to be treated with that drug.

The Drug

It will be understood that the essence of the present invention is the method of linking drug and antibody by means of the above-described malonate linkers, and that neither the drug nor the antibody is a limitation of the present invention. The malonate linkers of the present invention, accordingly, may be and are used beneficially when applied to drugs of any therapeutic or prophylactic purpose, limited only by the necessity for the drug to have a chemical function with which the malonate can link, and the necessity for the antibody to target a cell where the drug is beneficial. The methylene linking mechanism provided by the present invention calls for the drug to have a reactively available amino, hydroxy or thiol function. Further, of course, the drug must be of a nature such that reaction of that reactively available function with the linker does not destroy the activity of the drug.

Accordingly, the present linker invention may be used in connection with drugs of substantially all classes, including for example, antibacterials, antivirals, antifungals, anticancer drugs, antimycoplasmals, and the like. The drug conjugates so constructed are effective for the usual purposes for which the corresponding drugs are effective, and have superior efficacy because of the ability, inherent in the antibody, to transport the drug to the cell where it is of particular benefit.

U.S. Pat. No. 4,671,958 gives information about drugs and other compounds which may be subjected to drug conjugation, and the disclosure concerning drugs of that patent is herein incorporated by reference.

As stated, the drug is reacted through an amino, hydroxy or thiol function of it. Those terms are used in an expansive sense; that is, the term "amino group" includes amino groups which are part of carboxamides, hydrazides, carbamates and the like, as well as amino groups attached simply to a carbon-hydrogen structure. An amino group may have a third small substituent on it, so long as the group does not create steric hindrance which prevents reaction with the malonate structure. Such groups may be, for example, straight-chain alkyl groups and the like.

Similarly, a hydroxy or thiol group may be part of a carboxylic acid or thioic acid.

While the use of drugs of any chemical type and any therapeutic or prophylactic efficacy is included in the present invention, it is preferred to use drugs which have an amino function available for reaction. It is more preferred to use drugs wherein the amino group is part of a hydrazine or hydrazide moiety.

The most preferred efficacy class of drugs for use in the present invention is the class of cytotoxic drugs, particularly those which are used for cancer therapy. Such drugs include, in general, alkylating agents, antiproliferative agents, tubulin binding agents and the like. Preferred classes of cytotoxic agents include, for example, the daunomycin family of drugs, the vinca drugs, the mitomycins, the bleomycins, the cytotoxic nucleosides, the pteridine family of drugs, and the podophyllotoxins. Particularly useful members of those classes include, for example, doxorubicin, daunorubicin, aminopterin, methotrexate, methopterin, dichloromethotrexate, mitomycin C, porfiromycin, 5-fluorouracyl, 6-mercaptopurine, cytosine arabinoside, podophyllotoxin, etoposide, melphalan, vinblastine, vincristine, leurosidine, vindesine, leurosine, and the like. It will be understood that unimportant chemical modifications may be made by the ordinarily skilled chemist to the preferred and generally described compounds in order to make reactions of them more convenient.

It will also be understood that preferred conjugates are prepared from the preferred drugs.

A more highly preferred group of cytotoxic agents for use as drugs in the present invention includes the drugs of the following formulae.

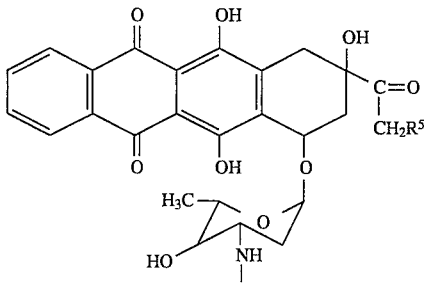

V wherein $R^5$ is hydrogen or hydroxy;

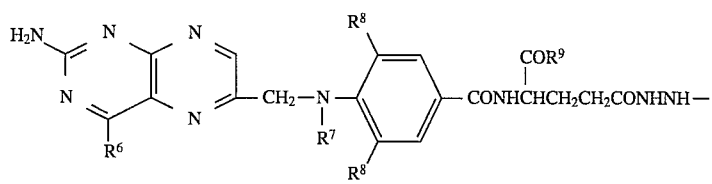

VI wherein $R^6$ is amino or hydroxy;

$R^7$ is hydrogen or methyl;

$R^8$ is hydrogen fluoro, chloro, bromo or iodo;

$R^9$ is hydroxy or a moiety which completes a salt of the carboxylic acid;

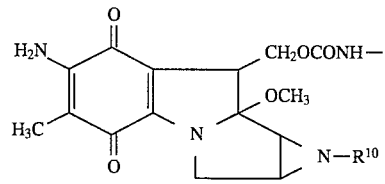

VII wherein $R^{10}$ is hydrogen or methyl;

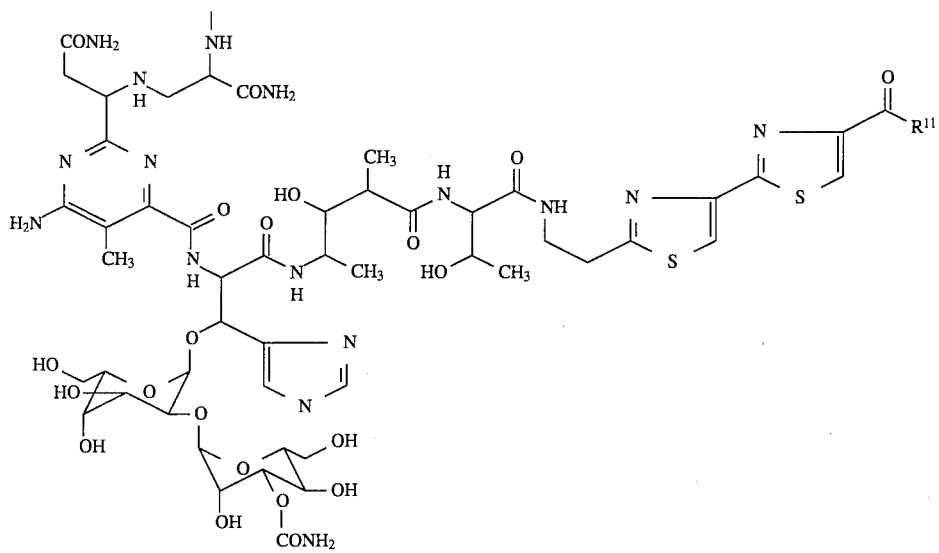

VIII wherein
R¹¹ is amino, $C_1$–$C_3$ alkylamino, di($C_1$–$C_3$ alkyl)amino or $C_4$–$C_6$ polymethylene amino;

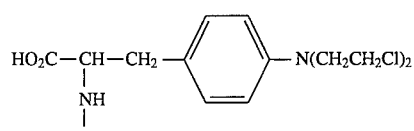

IX

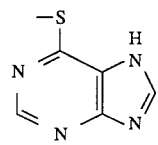

X

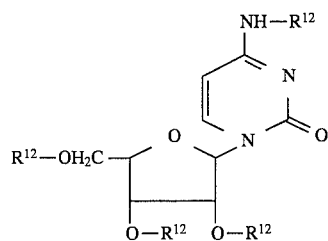

XI wherein
one of the $R^{12}$ moieties is a bond and the others are hydrogen;

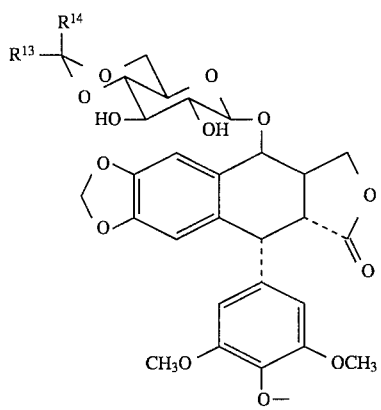

XII wherein $R^{13}$ is hydrogen or methyl;
$R^{14}$ is methyl or thienyl;

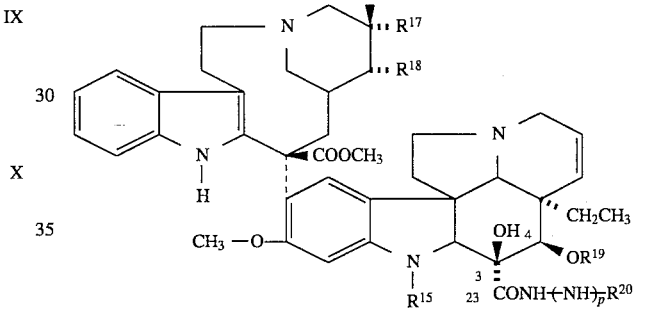

XIII wherein
$R^{15}$ is H, $CH_3$ or CHO; when $R^{17}$ and $R^{18}$ are taken singly, $R^{18}$ is H, and one of $R^{16}$ and $R^{17}$ is ethyl and the other is H or OH; when $R^{17}$ and $R^{18}$ are taken together with the carbons to which they are attached, they form an oxirane ring in which case $R^{16}$ is ethyl; $R^{19}$ is hydrogen, ($C_1$–$C_3$ alkyl)-CO, or chlorosubstituted ($C_1$–$C_3$ alkyl)-CO;
p is 0 or 1;
$R^{20}$ is a bond or ($C_2$–$C_4$ alkyl)-X;
X is —O—, —S— or —NH—;

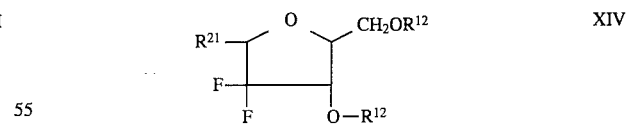

XIV wherein
$R^{21}$ is a base of one of the formulae

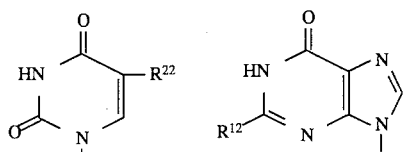

-continued

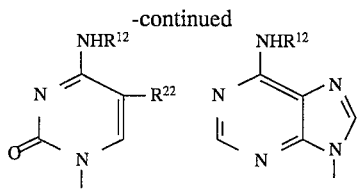

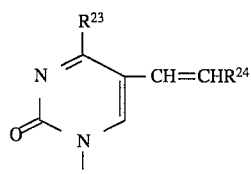

wherein be understood, is the compound of the formula above wherein $R^{15}$ is methyl, $R^{16}$ is ethyl, $R^{17}$ is hydroxy, $R^{18}$ is hydrogen, $R^{19}$ is acetyl, and the carbonyl group at $C_{23}$ is in the form of a methyl ester, rather than a carboxamide as shown above.

The following table represents a number of vinca drugs which illustrate those used in the present invention.

TABLE I

| $R^{15}$ | $R^{16}$ | $R^{17}$ | $R^{18}$ | $R^{19}$ | p | $R^{20}$ |
|---|---|---|---|---|---|---|
| H | H | $C_2H_5$ | H | H | 0 | — |
| $CH_3$ | $C_2H_5$ | OH | H | H | 0 | $(CH_2)_2O$— |
| CHO | $C_2H_5$ | H | H | $COCH_3$ | 1 | — |
| CHO | OH | $C_2H_5$ | H | $COC_2H_5$ | 1 | $(CH_2)_3S$— |
| $CH_3$ | $C_2H_5$ | Oxirane | | $COCH(CH_3)_2$ | 1 | $(CH_2)_4NH$— |
| H | $C_2H_5$ | H | H | $COCH_2Cl$ | 0 | $(CH_2)_2NH$— |
| $CH_3$ | $C_2H_5$ | Oxirane | | $COCHClCH_2Cl$ | 1 | $CH_2CH_2(CH_3)CH_2O$— |
| H | $C_2H_5$ | Oxirane | | $COCCl_3$ | 1 | $C(CH_3)_2CH_2O$— |
| CHO | OH | $C_2H_5$ | H | $CO(CH_2)_2CHCl_2$ | 0 | $C(CH_3)CH_2CH_2NH$— |
| $CH_3$ | H | $C_2H_5$ | H | H | 0 | $(CH_2)_2S$— |
| $CH_3$ | $C_2H_5$ | OH | H | H | 1 | $CH(CH_3)CH_2NH$— |

$R^{22}$ is hydrogen, methyl, bromo, fluoro, chloro or iodo;
$R^{23}$ is —$OR^{12}$; or —$NHR^{12}$;
$R^{24}$ is hydrogen, bromo, chloro or iodo.

In the above preferred formulae, the compounds of Formula V represent the daunomycin (or adriamycin) group of compounds; Formula VI represents the methotrexate group of compounds; Formula VII represents the mytomycins; Formula VIII represents the bleomycins; Formula IX represents melphalan; Formula X represents 6-mercaptopurine; Formula XI represents cytosine arabinoside; Formula XII the podophyllotoxins; Formula XIII represents the vinca drugs; and Formula XIV represents the difluoronucleosides.

Among the preferred drugs, the most preferred are the vinca drugs and the daunomycin family of drugs; another preferred class includes the vinca drugs, the daunomycin family and the methotrexate family.

Another class of preferred drugs includes 6-mercaptopurine, the difluoronucleosides and cytosine arabinoside. Still another class of preferred drugs includes the difluoronucleosides, the vinca drugs and the daunomycin drugs.

Another preferred group of the preferred drugs constitutes those which are linked through an amino group.

The vinca drugs used in the present invention are known in the art, particularly from the various patents and publications of Cullinan et al. and Trouet et al. Cullinan's U.S. Pat. No. 4,203,898 is particularly informative on the synthesis of the vinca drugs used in the present invention.

The most highly preferred drugs are the vinca compounds of Formula XIII above. It will be understood that the structural formula includes compounds which are, or are derivatives of, drugs having a number of different generic or trivial names. Accordingly, in order to simplify the complex nomenclature of the vinca drugs, they will be named in this document as derivatives of vinblastine. Vinblastine, it will The difluoronucleosides, taught by U.S. Pat. No. 4,692,434, afford a number of positions where reaction with the linking group is possible through amino or hydroxy groups. A particularly preferred drug of Formula XIV is 2'-deoxy-2',2'-difluorocytidine, which can also be named 1-(2-oxo-4-amino-1H-pyrimidin-1-yl)-2-desoxy-2,2-difluororibose. It will be understood that the compound may be reacted to form the conjugate at the 5'-hydroxy group, at the 3-hydroxy group, or at an amino group on the base.

Since the difluoronucleosides are relatively new in the art, a group of them will be mentioned to assure understanding.
1-(5-methyl-2,4-dioxo-1H,3H-pyrimidin-1-yl)-2-desoxy-2,2-difluororibose
1-(2,4-dioxo-1H,3H-pyrimidin-1-yl)-2-desoxy-2,2-difluororibose
1-(5-bromo-2,4-dioxo-1H,3H-pyrimidin-1-yl)-2-desoxy-2,2-difluororibose
1-(5-chloro-2,4-dioxo-1H,3H-pyrimidin-1-yl)-2-desoxy-2,2-difluororibose
1-(5-iodo-2,4-dioxo-1H,3H-pyrimidin-1-yl)-2-desoxy-2,2-difluororibose
1-(4-amino-5-chloro-2-oxo-1H-pyrimidin-1-yl)-2-desoxy-2,2-difluororibose
1-(4-amino-5-bromo-2-oxo-1H-pyrimidin-1-yl)-2-desoxy-2,2-difluororibose
1-(4-amino-2-oxo-1H-pyrimidin-1-yl)-2-desoxy-2,2-difluororibose
1-(4-amino-5-methyl-2-oxo-1H-pyrimidin-1-yl)-2-desoxy-2,2-difluororibose
1-[5-(2-bromovinyl)-4-hydroxy-2-oxo-1H-pyrimidin-1-yl]-2-desoxy-2,2-difluororibose
1-[4-amino-5-(2-bromovinyl)-2-oxo-1H-pyrimidin-1-yl]-2-desoxy-2,2-difluororibose
1-[4-amino-5-(2-iodovinyl)-2-oxo-1H-pyrimidin-1-yl]-2-desoxy-2,2-difluororibose 1-[5-(2-chlorovinyl)-4-hydroxy-2-oxo-1H-pyrimidin-1-yl]-2-desoxy- 2,2-difluororibose
1-[4-hydroxy-5-(2-iodovinyl)-2-oxo-1H-pyrimidin-1-yl]-2-desoxy-2,2-difluororibose
1-[4-amino-5-(2-chlorovinyl)-2-oxo-1H-pyrimidin-1-yl]-2-desoxy-2,2-difluororibose
1-(2-amino-6-oxo-1H,9H-purin-9-yl)-2-desoxy-2,2-difluororibose
1-(6-amino-9H-purin-9-yl)-2-desoxy-2,2-difluororibose
1-(5-fluoro-2,4-dioxo-1H,3H-pyrimidin-1-yl-2-desoxy-2,2-difluororibose
1-(2,4-dioxo-1H,3H-pyrimidin-1-yl)-2-desoxy-2,2-difluoroxylose
1-(5-bromo-2,4-dioxo-1H,3H-pyrimidin-1-yl)-2-desoxy-2,2-difluoroxylose
1-(5-chloro-2,4-dioxo-1H,3H-pyrimidin-1-yl)-2-desoxy-2,2-difluoroxylose
1-(5-iodo-2,4-dioxo-1H,3H-pyrimidin-1-yl)-2-desoxy-2,2-difluoroxylose
1-(4-amino-5-fluoro-2-oxo-1H-pyrimidin-1-yl)-2-desoxy-2,2-difluororibose
1-(4-amino-5-chloro-2-oxo-1H-pyrimidin-1-yl)-2-desoxy-2,2-difluoroxylose
1-(4-amino-2-oxo-1H-pyrimidin-1-yl)-2-desoxy-2,2-difluoroxylose
1-(4-amino-5-fluoro-2-oxo-1H-pyrimidin-1-yl)-2-desoxy-2,2-difluoroxylose
1-(4-amino-5-methyl-2-oxo-1H-pyrimidin-1-yl)-2-desoxy-2,2-difluoroxylose
1-[5-(2-bromovinyl)-4-hydroxy-2-oxo-1H-pyrimidin-1-yl]-2-desoxy- 2,2-difluoroxylose
1-[4-amino-5-(2-bromovinyl)-2-oxo-1H-pyrimidin-1-yl]-2-desoxy-2,2-difluoroxylose
1-[4-amino-5-(2-iodovinyl)-2-oxo-1H-pyrimidin-1-yl]-2-desoxy-2,2-difluoroxylose
1-[5-(2-chlorovinyl)-4-hydroxy-2-oxo-1H-pyrimidin-1-yl]-2-desoxy- 2,2-difluoroxylose
1-[4-hydroxy-5-(2-iodovinyl)-2-oxo-1H-pyrimidin-1-yl]-2-desoxy-2,2-difluoroxylose
1-4-amino-5-(2-chlorovinyl)-2-oxo-1H-pyrimidin-1-yl]-2-desoxy-2,2-difluoroxylose
1-(2-amino-6-oxo-1H,9H-purin-9-yl)-2-desoxy-2,2-difluoroxylose
1-(6-amino-9H-purin-9-yl)-2-desoxy-2,2-difluoroxylose.

Particularly preferred vinca drugs are those described by the following limitations. It will be understood that the various individual limitations which follow can be combined to form further, more limited preferred classes.

A. $R^{15}$ is methyl;
B. $R^{15}$ is hydrogen or formyl;
C. $R^{16}$ is ethyl;
D. $R^{18}$ is hydrogen;
E. One of $R^{16}$ and $R^{17}$ is ethyl and the other is hydrogen or hydroxy;
F. $R^{17}$ is hydroxy;
G. $R^{19}$ is hydrogen;
H. $R^{19}$ is acetyl;
I. $R^{19}$ is $C_1$–$C_3$ alkyl-CO;
J. p is 1;
K. $R^{20}$ is a bond;
L. $R^{20}$ is $(C_2$–$C_4$ alkyl)-X;
M. p is 0;
N. X is —NH—;
O. X is —O— or —S—
P. $R^{20}$ is ethoxy, ethylthio or ethylamino;
Q. $R^{20}$ is a bond;
R. $R^{20}$ is $(C_2$–$C_4$ alkyl)-NH—.

The Intermediates

The intermediate malonates of the present invention are the intermediates which are reacted with the antibody and with the drug. Thus, the intermediate malonates are the precursors of the linker which joins the antibody and the drug; accordingly, the preferred intermediate malonates confer their structures on the preferred conjugates.

The intermediates are derivatives of malonic acid, and are prepared according to processes known or readily imagined by those of ordinary organic chemical skill. A group of the compounds will be described, however, by reference to the variable groups, in order to assure the reader's understanding.

TABLE II

| n | $R^2$ | Y | $R^3$ | $R^4$ |
|---|---|---|---|---|
| 1 | OH | O | N-succinimidyloxy | $OCH_3$ |
| 4 | ONa | O | N-phthalimidyloxy | $OC_2H_5$ |
| 6 | OLi | NH | N-benzotriazolyloxy | $OCH(CH_3)_2$ |
| 2 | OK | $NCH_3$ | N-piperidinyloxy | $O(CH_2)_3CH_3$ |
| 3 | $OCH_2CH_3$ | O | $OCH_2CH=CH_2$ | $OC_2H_5$ |
| 7 | $OCH(C_6H_5)_2$ | O | $OCH_2CH=CHC_6H_5$ | $OCH_3$ |
| 1 | $OCH_2C_6H_4OCH_3$ | O | $ONHCH_3$ | $OCH(CH_3)_2$ |
| 8 | OH | NH | $ON(C_3H_7)_2$ | $O(CH_2)_2CH_3$ |
| 6 | $OCH_2CCl_3$ | NH | OH | $O(CH_2)_3CH_3$ |
| 5 | $OC(CH_3)_3$ | $NC_2H_5$ | $OCH_2CCl_3$ | $OCH_3$ |
| 7 | $OSi(CH_3)_3$ | $NC_2H_5$ | $OC(CH_3)_3$ | $OCH_3$ |
| 3 | $ON(C_2H_5)_3$ | O | $ON(CH_3)_3C_6H_5$ | $OC_2H_5$ |
| 4 | $ON((CH_2CH_2OH)_2$ | O | $ON[(CH_2)_3CH_3]_4$ | $OC_2H_5$ |
| 6 | $OCH_2OCH_3$ | NH | $ON(CH_3)_3C_2H_5$ | $OC_2H_5$ |
| 2 | $OCH_2O(CH_2)_2OCH_3$ | NH | $ON(C_2H_5)_3CH_2C_6H_5$ | $OCH(CH_3)CH_2CH_3$ |
| 1 | $OCH_2COC_6H_5$ | O | OH | $OCH_2CH(CH_3)_2$ |
| 8 | $OCH_2COC_6H_4Br$ | NH | ONa | $OCH_3$ |
| 6 | $OCH_2CH=CH_2$ | O | OLi | $OC_2H_5$ |
| 5 | $OCH_2CH=CHC_6H_5$ | O | OK | $OCH_2(CH_3)_2$ |
| 3 | $ONHCH_3$ | $NCH_3$ | $OSi(CH_3)_3$ | $OC_2H_5$ |
| 4 | $ON(C_3H_7)_2$ | $NC_2H_5$ | $ON(C_2H_5)_3$ | $OCH_3$ |
| 2 | $ON(CH_3)_3C_6H_5$ | O | $ON(CH_2CH_2OH)_2$ | $OCH(CH_3)_2$ |
| 3 | $ON[(CH_2)_3CH_3]_4$ | O | $OCH_2OCH_3$ | $OC_2H_5$ |

TABLE II-continued

| n | R² | Y | R³ | R⁴ |
|---|---|---|---|---|
| 1 | ON(CH₃)₃C₂H₅ | NH | OCH₂O(CH₂)₂OCH₃ | OC₂H₅ |
| 4 | ON(C₂H₅)₃CH₂C₆H₅ | O | OCH₂COC₆H₅ | OC₂H₅ |
| 2 | OH | O | OCH₂COC₆H₄Br | OCH₃ |
| 7 | ON(C₂H₅)₂ | NH | OCH₂CH₃ | OCH₃ |
| 3 | OCH₂CH₂Si(CH₃)₃ | NC₂H₅ | OCH(C₆H₅)₂ | OCH(CH₃)₂ |
| 6 | OH | O | OCH₂C₆H₄OCH₃ | OC₂H₅ |
| 1 | NH₂ | O | OH | OC₂H₅ |
| 3 | NHCH₃ | NH | OK | OCH₃ |
| 2 | N(C₂H₅)₂ | NH | ONHCH₃ | OC₂H₅ |
| 1 | N(CH₃)(C₃H₇) | NCH₃ | OSi(CH₃)₃ | OC₃H₇ |
| 1 | NHCH₂C₆H₅ | NC₂H₅ | OC₂H₅ | OC₂H₅ |
| 2 | N(CH₂)₄ | NH | OCH₂C₆H₅ | OCH₃ |
| 2 | NH(CH₂)₂N(C₂H₅)₂ | O | OLi | OC₂H₅ |
| 3 | NH(CH₂)₃N(CH₂)₅ | O | ONHCH₃ | OCH₃ |
| 2 | NH(CH₂)₂N(CH₃)(CH₂C₆H₅) | O | ON(C₂H₅)₃ | OC₂H₅ |

Various subgroups of the intermediate malonates are preferred, as follows. It will be understood that the preferred subgroups may be combined to form further, more limited preferred groups.

A. R⁴ is C₂-C₃ alkoxy;
B. R⁴ is ethoxy;
C. R² is hydroxy or a salt-forming moiety;
D. R² is a protecting group;
E. R² is a protecting group which is linked through an oxygen atom;
F. R² is a protecting group which is linked through a nitrogen atom;
G. R² is an alkoxy group;
H. R² is an amino or alkylamino group;
I. R³ is an activating group;
J. R³ is a protecting group;
K. R³ is hydroxy or a salt-forming moiety;
L. R³ is N-succinimidyloxy, N-phthalimidyloxy or N-benzotriazolyloxy;
M. n is from 1 to about 3;
N. n is from 1 to about 6;
O. n is from about 3 to about 8;
P. n is from about 5 to about 8.
Q. Y is —O—;
R. Y is —NH—;
S. Y is —NCH₃— or —NC₂H₅—.

The Modified Antibodies

The modified antibodies are intermediates for the preparation of the conjugates, which consist of the entire conjugate, lacking the drug. They are prepared by reacting the intermediate malonate with the antibody, according to processes described below in the synthesis section of this document.

The preferred modified antibodies are made up of preferred variable groups of the malonate intermediates, reacted with preferred antibodies. A group of typical modified antibodies will be mentioned here, to assure understanding. Because of the difficulty in nomenclature of these complicated molecules, the compounds will be identified by the identity of their component variables, rather than by chemical name. The antibodies mentioned here are known to the immunological art.

TABLE III

| n | m | R⁴ | R¹ | Ab | Y |
|---|---|---|---|---|---|
| 1 | 3 | OCH₃ | OC₂H₅ | L/1C2,F(ab')₂ | NH |
| 3 | 5 | OC₂H₅ | OCH₂OCH₃ | KS1/4 | NH |
| 7 | 7 | OC₂H₅ | OCH₂SCH₃ | 5E9C11 | NCH₃ |
| 2 | 6 | OCH(CH₃)₂ | OCH₂OCH₂C₆H₅ | B72.3 | NC₂H₅ |
| 4 | 4 | O(CH₂)₃CH₃ | OCH(CH₃)COC₆H₅ | OKT4 | O |
| 6 | 2 | OC₂H₅ | OCH₂CCl₃ | YOL1-34 | O |
| 8 | 1 | OCH₃ | OCH₂CH₂Si(CH₃)₃ | B1011 | NH |
| 5 | 8 | OCH(CH₃)C₂H₅ | OCH₂CH₂SO₂C₆H₄CH₃ | 8.14.49 | O |
| 1 | 9 | OCH₂CH(CH₃)₂ | OC(CH₃)₃ | B1018 | O |
| 2 | 6 | OC₂H₅ | Ocyclohexyl | GS-1.A | O |
| 4 | 10 | OCH₃ | OCH(CH₃)₂ | KP9.2 | NH |
| 3 | 5 | O(CH₂)₂CH₃ | OCH₂CH=CHC₆H₅ | p97 | NCH₃ |
| 6 | 4 | OCH(CH₃)₂ | OC₆H₅ | TFS-2 | NC₂H₅ |
| 7 | 3 | OCH₃ | OC(C₆H₅)₃ | D83.21 | NH |
| 5 | 4 | OC₂H₅ | OCH₂C₆H₄OCH₃ | A6H | O |
| 8 | 6 | O(CH₂)₃CH₃ | OSi(CH₃)₃ | B6.2 | O |
| 2 | 3 | OC₂H₅ | OCH₃ | 14.95.55 | O |
| 4 | 8 | OCH₃ | OC₂H₅ | 791T/48 | O |
| 2 | 5 | OC₂H₅ | N(CH₃)₂ | B1018 | NCH₃ |
| 1 | 6 | OCH₃ | NH(CH₂)₂N(CH₃)₂ | KS1/4 | NH |
| 2 | 4 | OC₂H₅ | N(CH₂)₄ | L/1C2 | NH |
| 3 | 5 | OC₂H₅ | N(C₂H₄)₂ | 5E9C11 | O |

The Derivatized Drugs

The derivatized drugs of the present invention are intermediates, formed by reacting the drug with the intermediate malonate, which are used to form the conjugates by reaction with the antibody. In the definitional formula above of the derivatized drugs, the broad definitions and the preferred meanings of the groups R, $R^1$, $R^3$, Y and n are as have been discussed above, and it will be clearly understood that any desired or preferred derivatized drug is prepared by choosing the desired definitions of the different variable groups, particularly preferred definitions of the groups of the intermediate malonates. The derivatized drugs are prepared by methods discussed in the synthesis section below.

Synthesis

It will be understood by organic chemists that, in many steps of the present synthesis, it will be necessary to protect various reactive functions on the starting compounds and intermediates while desired reactions are carried out with other reactive functions. After the reactions are over, it will accordingly be necessary to remove those protecting functions, in general. Such protection and deprotection steps are entirely conventional in organic chemistry, and will not necessarily be explained in full in this document. It will be noted, however, that Greene's textbook on protective groups, cited above, fully explains protective groups for all of the commonly found reactive functions, including hydroxy groups, thiol groups, amino groups and the like, and outlines the methods for placing and removing those protective groups.

Synthesis of the Intermediate Malonates

An ordinarily skilled organic chemist can prepare any of the intermediate malonates from general knowledge and common literature. The preferred method for preparing them, however, starts with a malonic acid derivative where the carboxylic acid protecting group, $R^2$, is on one of the carboxy groups. The other carboxy group may be substituted the same or differently. If it is different, the non-$R^2$ group must be more easily removed than the $R^2$ group. The starting compound is reacted with a haloalkanoate or aminoalkanoate, where the length of the alkyl chain provides n methylene groups. A haloalkanoate is used to make intermediates where Y is oxygen, to create the ester linkage. In this case the halogen atom (or other good leaving group) is at the end of the chain. An aminoalkanoate, where the amino is at the end of the chain, is used to make the intermediates where Y is amino. The ester portion of the alkanoate is an acid protecting group, $R^3$.

The reaction is carried out by removing the non-$R^2$ group of the starting compound, and reacting the carboxylic acid radical thus formed with the alkanoate. The reaction has been successfully carried out by initial reduction, for example, by use of a hydrogenation catalyst in the presence of cyclohexadiene. Alternatively, hydrogenation may be used in the presence of an appropriate catalyst, such as a noble metal catalyst.

The reaction may also be carried out by decomposing the non-$R^2$ ester with a strong base, particularly lithium hydroxide in an aqueous solvent such as aqueous acetone. When the carboxylic acid radical has been formed, the haloalkanoate is added and the intermediate malonate forms quite quickly, particularly in the presence of an acid scavenger. However, when the reaction is with an aminoalkanoate, the carboxylic acid radical should be activated by adding one of the activating groups described above, before the reaction to form the malonamate.

The reaction above forms the intermediate malonate, with an acid protecting group at $R^3$, but missing the moiety $R^4$—CH=. That group, an alkoxymethylene group, is inserted by reacting the first intermediate with an appropriate alkyl orthoformate, in the presence of a Lewis acid, such as zinc chloride. The reaction is carried out at an elevated temperature, in the range of 100°–200°, and is complete in a few hours time.

In the above reactions, as well as in the other processes described below, no unusual excess amounts of starting compounds are necessary. As is ordinarily the case in organic chemistry, it is advisable to use a moderate excess of comparatively inexpensive reactants, in order to assure that more expensive ones are fully consumed. This rule is particularly true in the case of the reactions with antibodies themselves, which typically are quite expensive and difficult to prepare and purify. In general, however, amounts of excess reactants may be chosen with regard to maximizing the economy of the processes, bearing in the mind the cost of the ingredients as well as throughput of the equipment, and it is unnecessary to use excess amounts merely to force the reactions to occur.

Reactions with Drugs

The intermediate malonates are reacted with drugs under conditions which will allow the alkoxy group $R^4$ to be cleaved, and the remaining methylene group to react with the reactive amino, hydroxy or thiol function of the drug. In general, the reactions are carried out under mild conditions, from about 0° to about 50°, in organic solvents which will not react with either of the reactants or in aqueous mixtures of such organic solvents, and usually in the presence of mild bases such as alkali metal bicarbonates, carbonates, and hydroxides. The reactions are quantitative, in general, and require no unusual excess amounts. Isolation of the product may, however, require chromatography under high pressure or other sophisticated procedures, because it usually is important to purify the derivatized drug with considerable care. Since the derivatized drug is reacted with the antibody to complete the conjugate, any reactive impurity which accompanies the derivatized drug will consume reactive sites on the antibody, thereby wasting expensively prepared antibody.

In a case where the drug has multiple reactive sites, such as the nucleosides which have multiple hydroxy groups, it usually is necessary to block the drug's reactive groups which are not intended to be used. Such blocking is done with protective groups as has been discussed and presents no particular difficulty to the organic chemist.

The carboxylic acid protecting group, $R^3$, may be removed from the intermediate malonate either before or after it is reacted with the drug. If it is necessary to use protecting groups on the drug, it may well be possible for those groups to be removable under the same conditions which remove the $R^3$ protecting group, thereby obtaining double use from the deprotecting step.

Synthesis of the Modified Antibodies

The antibodies are reacted with the intermediate malonates in the activated form, where the $R^3$ group of the intermediate malonate is a carboxylic acid activating group such as have been explained above. The activating groups are placed on the carboxylic acids (where $R^3$ is hydrogen) by use of conventional esterification reagents such as carbodiimides, particularly dicyclohexylcarbodiimide. Such reactions are carried out after an acid protecting $R^3$ group has been removed by appropriate methods, depending on the protecting group in use. Reactions with activating groups are carried out in inert organic solvents, such as dioxane, tetrahydrofuran, chlorinated hydrocarbons and the like, and may be performed at moderate temperatures in the range of about 0°–50°.

The primary concern in choosing the conditions under which to react the intermediate malonate with the antibody is maintaining the stability of the antibody. The reaction must be carried out in aqueous medium of a composition which will not harm the antibody. A particularly suitable aqueous medium is a borate buffer solution, in which the concentration of borate ion is in the range of about 0.1–0.5 molar. Another appropriate aqueous medium in which to carry out the reaction is physiological buffered saline solution. The pH of the reaction medium should be slightly basic, in the range of about 7–9. While the reaction medium should be aqueous, the presence of small amounts of organic solvents is not harmful, and may be quite convenient. For example, it may be most advantageous to dissolve the intermediate malonate in a small amount of organic solvent, for example, dimethylformamide, acetonitrile, tetrahydrofuran, dioxane, or a glycol ether, and add the organic solution to the antibody solution in the aqueous medium.

In general, it will be necessary to operate the reaction at a comparatively low concentration because the solubility of antibodies is generally not great. For example, the concentration of the antibody is usually in the range of about 5–25 mg per ml of aqueous medium.

As described above, from 1 to about 10 moles of linker and drug are attached to each mole of antibody. In order to obtain that conjugation ratio, it is usually necessary to use an excess quantity of linker intermediate. The reactivity of antibodies and active esters under acylating conditions is somewhat variable, but in general, from about 5 to about 15 moles of linker intermediate per mole of antibody are used in the process.

The acylation reaction is allowed to proceed from a few minutes to a few hours, at temperatures in the range from about 0° to about 40°. Obviously, elevated temperatures may be injurious to the antibody and it is more advisable to operate at low temperatures, particularly since the reaction is inherently quick.

When the derivatized antibody, having the linker groups in place, has been prepared, the reaction mixture can be chromatographed by conventional procedures, as shown in the examples below, to separate the derivatized antibody from unreacted linker intermediate.

Synthesis of the Conjugates

When a modified drug is made, and is reacted with the antibody as the final step in preparing the conjugate, the above observations concerning the precautions pertinent to reactions with antibodies are entirely applicable. The same principles govern the choice of the ratio between the amount of antibody and the amount of derivatized drug. In general, the reaction conditions must be chosen with regard to the stability of the antibody, since the drug can be expected to tolerate any conditions which the antibody will tolerate.

The derivatized drug must be converted into the activated form, where $R^3$ is a carboxylic acid activating group, as described above under the synthesis of the modified antibodies.

On the other hand, when a modified antibody is made, and reaction with the drug is the final step, precautions to assure the stability of the antibody must be observed.

Accordingly, the preferred process is to make a derivatized drug, and to react it as the final step with the antibody. Reaction of the modified antibody with the drug must be carried out at comparatively low temperatures, such as from about 0° to about 40°, and in a medium which the antibody can tolerate. For example, a particularly useful reaction medium is borate buffer, especially 0.1–0.5 molar sodium borate buffer at a pH in the range from about 7 to about 9. The reaction also may be carried out, however, in borate buffer, slightly acid phosphate buffers, physiological buffered saline and the like. Small amounts of organic solvents in the reaction medium are not harmful, as discussed above, so long as the solvents do not have a tendency to damage the antibody.

Finally, the drug conjugate is purified and isolated, customarily by chromatographic methods. It may be possible to elute a conjugate from the chromatography medium in a concentration which is appropriate for administration to patients. Customarily, however, the conjugate will be purified by chromatography, eluting with any convenient solvent, but most preferably with physiological buffered saline, in the highest concentration which its solubility permits. The eluant will customarily be lyophilized, to provide the conjugate in a dry, stable form which can be safely stored and shipped, and eventually can be reconstituted with sterile water for administration.

Synthesis of the various intermediates and the conjugates of the present invention is further explained by the following preparations and examples.

Preparation 1

Benzyloxycarbonylmethyl ethyl malonate

To a round bottom flask equipped with a stirrer was added 400 ml of acetone and 50 g of diethyl malonate. When solution had been obtained, 200 ml of water was added, followed by 156 ml of 2N lithium hydroxide solution. The mixture was stirred at ambient temperature for 30 minutes, and then was concentrated under vacuum to a solid. To it was added 350 ml of dimethylsulfoxide, and the mixture was stirred while 71.5 g of benzyl 2-bromoacetate was added. The mixture was then stirred for 3 hours at ambient temperature, and it was then extracted with 1000 ml of ethyl acetate with brine, and the extract was washed twice with brine. The extract was dried over sodium sulfate, filtered and concentrated under vacuum overnight to give 76.4 g of viscous liquid which was distilled at 0.1 mm mercury to give 18.8 g of the desired intermediate in substantially pure form.

Preparation 2

Benzyloxycarbonylmethyl ethyl malonate

A 5 g portion of palladium on carbon hydrogenation catalyst was suspended in 60 ml of absolute ethanol in a flask equipped with a stirrer, and 25 g of benzyl ethyl malonate and 16 ml of 1,4-cyclohexadiene were added. The mixture was stirred for 1.5 hours, and it was then filtered and the filtrate was concentrated under vacuum to a syrup. Sixty ml of dimethylformamide and 15.6 ml of triethylamine were added to the residue, followed by 17.7 ml of benzyl 2-bromoacetate. The mixture was stirred at ambient temperature for one hour, and it was then extracted with 600 ml of ethyl acetate with brine, and the extract was washed with saturated sodium bicarbonate solution, with brine, with 10% citric acid solution, with brine, and again with saturated sodium bicarbonate and brine. The washed extract was dried over magnesium sulfate, filtered and concentrated under vacuum to obtain 28.2 g of pure desired intermediate, which was 1-spot material by thin layer chromatography, eluting with 1:1 ethyl acetate:hexane, Rf=0.55. Mass spectroscopy gave m/e=280.

Preparation 3

Benzyloxycarbonylmethyl ethyl 2-ethoxymethylenemalonate

Ten g of the product of Preparation 1 was dissolved in 11.1 ml of acetic anhydride in a flask equipped with a stirrer, and 7.8 ml of triethylorthoformate was added. The mixture was heated for 6.5 hours at 140°–50°, and the volatiles were then removed under vacuum. The residue was dissolved in 11.1 ml of acetic anhydride and 7.8 ml of triethylorthoformate, and 50 mg of zinc chloride was added. The mixture was then heated under reflux, 140°–150° for 16 hours, and was then cooled and extracted into 600 ml of ethyl acetate with brine and washed with two portions of brine. The washed extract was dried over magnesium sulfate, filtered and concentrated, and the residue was dissolved in a minimum amount of ethyl acetate and the solution was made turbid with hexane. The solution was poured through a funnel full of silica gel, which was eluted with 1 liter of 10% ethyl acetate in hexane, and then with 1 liter of 20% ethyl acetate in hexane. The desired product was obtained in two additional liters of 20% ethyl acetate in hexane, which was concentrated under vacuum to obtain 4.9 g of colorless syrup which was essentially pure desired product.

Analysis Calculated: C, 60.71; H, 5.99; Found: C, 60.98; H, 6.03.

Preparation 4

Carboxymethyl ethyl 2-ethoxymethylenemalonate

One g of palladium on carbon hydrogenation catalyst was suspended in 15 ml of absolute ethanol in a flask equipped with a stirrer, and to it was added a solution of 4.9 g of the product of Preparation 3 in 10 ml of ethanol, followed by 2.8 ml of 1,4-cyclohexadiene. The mixture was stirred for 5 minutes, and was then heated to 45°, at which point it became exothermic. The heat was then turned off, and the mixture was stirred for 45 minutes, at which time it had reached ambient temperature. The mixture was then filtered, and was concentrated under vacuum to obtain 3.6 g of a yellow liquid, which was identified by mass spectroscopy as the desired intermediate product. m/e=246.

Preparation 5

Doxorubicin adduct of carboxymethyl ethyl 2-methylenemalonate

The product of this preparation is the adduct wherein doxorubicin is joined through the amino group of the daunosamine ring to the methylene of the intermediate malonate.

To a round bottom flask was added 134 mg of doxorubicin hydrochloride and 8.5 ml of dimethylformamide, and 1 ml of water was added to dissolve the drug. A 264 mg portion of the product of Preparation 4 was added, as a solution in 0.5 ml of dimethylformamide, and the mixture was stirred for 10 minutes. Then a solution of 115 mg of sodium bicarbonate in 1.25 ml of water was added, and the mixture was stirred for 2 hours at ambient temperature. Then the volatiles were removed under vacuum and the residue was dissolved in a minimum amount of 0.1M sodium acetate buffer at pH 5.4. The solution was applied to a C18 (J. T. Baker, Phillipsburg, N.J.) flash chromatography column, 1.75×6 cm, and the column was eluted with acetate buffer containing increasing amounts of methanol. The desired product was obtained in the fractions containing 50% and more of methanol, and the product-containing fractions were pooled and concentrated under vacuum. The residue was dissolved in several ml of water and was applied to the same column, which was eluted with 40 ml of water, then with 80 ml of 50% aqueous methanol and then with 20 ml of methanol. The desired product was in the fractions eluted with 50% methanol, which were pooled and concentrated under vacuum. The residue was dissolved in a minimum amount of methanol, a five fold volume of benzene was added, and the solution was frozen and lyophilized overnight to obtain 146 mg of an orange solid, m/e=744 by FAB mass spectroscopy. The product was shown to be pure by high performance liquid chromatography analysis, using a C18 radial pack column at 5 ml/minute of 70% aqueous methanol containing 3% of ammonium acetate.

Preparation 6

Doxorubicin adduct of ethyl N-succinimidoxycarbonylmethyl 2-methylenemalonate

To a round bottom flask equipped with a drying tube and stirrer was added 17.6 mg of the product of Preparation 5, dissolved in 1.5 ml of dry dimethylformamide. The solution was cooled to −5°, and 5.2 µl of N-methylmorpholine was added in 0.1 ml of dry dimethylformamide. The mixture was stirred at −5° for 5 minutes, and then 6.14 ml of isobutyl chloroformate was added in 0.1 ml of dry dimethylformamide and the mixture was stirred for 30 minutes more at constant temperature. Then 5.45 mg of N-hydroxysuccinimide was added in 0.1 ml of dry dimethylformamide, and the mixture was stirred for 20 hours while it warmed to ambient temperature. It was then concentrated under vacuum to a red residue, which was dissolved in a minimum volume of dichloromethane, and applied to a silica gel column, 0.75×4 cm, equilibrated with dichloromethane. The column was eluted with 50 ml of dichloromethane, and then with 10% isopropanol in dichloromethane. The second eluant was concentrated under vacuum, and the residue was dissolved in a minimum volume of isopropanol to which a small amount of benzene was added. The solution was frozen and lyophilized to obtain 15.9 mg of the desired product, m/e=742. The identity was confirmed by nuclear magnetic resonance spectroscopy (NMR) in $CDCl_3$ on a 300 mHz instrument, which showed the N-hydroxysuccinimide signal at 2.8 ppm.

EXAMPLE 1

Conjugate of antibody 007B with doxorubicin adduct of carbonylmethyl ethyl 2-methylenemalonate Antibody 007B is produced by a hybridoma which is a subclone derived from the hybridoma producing the antibody KS1/4, which is discussed above in the antibody section of this document. A 508 µl portion of a solution containing 19.7 mg/ml of that antibody in 0.34M sodium borate buffer at pH 8.6 was added to a 3-ml vial equipped with a stirrer. A 0.56 mg portion of the product of Preparation 6 in 56.4 µl of dried dimethylformamide was added to the antibody solution at ambient temperature, and was stirred for two hours. The mixture was then centrifuged at ambient temperature to throw down a red pellet and the supernatant was applied to a 1.75×25 cm Sephadex G-25M column (Pharmacia, Inc., Piscataway, N.J.) equilibrated with physiological phosphate buffered saline. The column was eluted with the same buffer, and the first peak off the column was collected. That fraction was filtered through a Millex-GV (Millipore, Bedford, Mass.) 0.22 µ filter, and was stored at 4° for three days. It was then filtered again in the same manner and evaluated by ultraviolet (U.V.) spectrophotometry, which showed a concentration of antibody of 1.54 mg/ml, indicating a recovery of 7.6 mg of conjugate. The conjugation ratio was 2.2 moles of drug per mole of antibody.

EXAMPLE 1A

Conjugate of antibody 007B with doxorubicin adduct of carbonylmethyl ethyl 2-methylenemalonate The process of Example 1 was followed, starting with 7.5 mg of antibody and 1.0 mg of the product of Preparation 6. The recovered conjugate amounted to 4.94 mg, having a conjugation ratio of 3.1 moles per mole, as a solution of concentration 1.10 mg/ml.

EXAMPLE 2

Conjugate of antibody HB21 with doxorubicin adduct of carbonylmethyl ethyl 2-methylenemalonate Antibody HB21 is produced by the hybridoma identified as ATCC HB21. A 17.5 mg portion of antibody HB21, in 0.875 ml of the borate buffer mentioned in Example 1 was added to a 3 ml vial equipped with a stirrer, and to it was added 1.3 mg of the product of Preparation 6, dissolved in 97.2 µl of dry dimethylformamide. The reaction was stirred, and the conjugate was isolated as described in Example 1, to obtain 14.9 mg of conjugate, at a concentration of 2.57 mg/ml, having a conjugation ratio of 3.8.

EXAMPLE 2A

Conjugate of antibody HB21 with doxorubicin adduct of carbonylmethyl ethyl 2-methylenemalonate The process of Example 2 was followed, starting with 12 mg of antibody and 1.30 mg of the product of Preparation 6. The filtered product solution was concentrated by vacuum dialysis to obtain 0.82 ml of solution, containing 3.25 mg of conjugate at a conjugation ratio of 4.5 moles per mole.

EXAMPLE 2B

Conjugate of antibody HB21 with doxorubicin adduct of carbonylmethyl ethyl 2-methylenemalonate The process of Example 2A was followed, starting with 12 mg of antibody and 2.60 mg of the product of Preparation 6. The product was 0.72 ml of solution, containing 1.37 mg of conjugate at a conjugation ratio of 5.6 moles per mole.

EXAMPLE 3

Conjugate of antibody L4KS with doxorubicin adduct of carbonylmethyl ethyl 2-methylenemalonate Antibody L4KS, as described by Starling et al., *J. Cell. Biochem. Supp.*, 11B, 1982 (1987), was dialyzed into 0.34M sodium borate buffer at pH 8.6 to provide 17.5 mg of antibody in 0.875 ml of buffer. To it was added 1.3 mg of the product of Preparation 6 in 97.2 µl of dry dimethylformamide. The reaction was carried out, and product was isolated, as described in Example 1, to obtain 11.6 mg of conjugate at a concentration of 2 mg/ml. The conjugation ratio was 2.6 moles per mole.

EXAMPLE 3A

Conjugate of antibody L4KS with doxorubicin adduct of carbonylmethyl ethyl 2-methylenemalonate The process of Example 3 was repeated, starting with 10 mg of antibody and 0.59 mg of the product of Preparation 6. The product solution was concentrated by vacuum dialysis to obtain 1.16 ml of solution containing 4.03 mg of conjugate at a conjugation ratio of 2.9.

Preparation 7

Production of L/1C2 antibodies

Vials of frozen L/1C2 hybridomas are obtained from the American Type Culture Collection, under the accession number HB9682. Viable cells are recovered by thawing the contents of a vial in a 37° C. water bath while swirling the vial. The cell suspension is then diluted 1:2 with balanced salt solution (Grand Island Biological Company (GIBCO), 3175 Staley Road, Grand Island, N.Y. 14072) and the suspension is centrifuged through a serum underlay to partition the cells from the cryogenic medium. The supernatant is aspirated, and the cells in the cell pellet are suspended in culture medium (Ventrex HL-1, Ventrex Laboratories, Portland, Me.) supplemented with 10% fetal calf serum, 2 mM L-glutamine (GIBCO) and 50 µg/ml gentamicin sulfate (GIBCO)) in T75 tissue culture flasks, in 5% carbon dioxide at 37° C. Supernatants from nearly confluent cultures are collected and residual cells are removed by centrifugation. Antibody is purified from the cell free supernatant by passing over a Protein A Sepharose column (Pharmacia). Antibody binds to the column and culture medium is washed free in 0.01M sodium phosphate at pH 8.0. Antibody is then eluted from the column with 0.1M sodium phosphate buffer at pH 3.5. Eluted antibody is immediately neutralized with 1M Trizma buffer (Sigma, St. Louis, Mo.) at pH 7.4 and dialyzed and concentrated in a vacuum dialyzer (Bio-Molecular Dynamics, Beaverton, Oreg.) containing 0.01M sodium phosphate pH 7.4 plus 0.15M sodium chloride. Antibody preparations are sterilized by filtration through 0.2 µm pores and stored at 4° C. until used.

EXAMPLE 4

Conjugate of antibody L/1C2 with doxorubicin adduct of carbonylmethyl ethyl 2-methylenemalonate A 10.1 mg portion of antibody L/1C2, in 0.94 ml of 0.34M sodium borate buffer was combined with 0.85 mg of the product of Preparation 6 in 54.7 µl of dried dimethylformamide. The reaction mixture was stirred at ambient temperature for 1.5 hours, and the product was then isolated as described in Example 1, and the resulting solution was vacuum dialyzed for about 16 hours at 4° against 5 liters of physiological phosphate buffered saline, to obtain 9.16 mg of conjugate, at a concentration of 5.33 mg/ml. The conjugation ratio was 1.7 moles per mole.

EXAMPLE 4A

Conjugate of antibody L/1C2 with doxorubicin adduct of carbonylmethyl ethyl 2-methylenemalonate The process of Example 4 was repeated, omitting the dialysis step, starting with 24 mg of antibody and 1.75 mg of the product of Preparation 6. An 8.56 mg portion of conjugate was recovered, in 2.69 ml of solution, at a conjugation ratio of 2.8.

Preparation 8

Benzyloxycarbonylpentyl ethyl malonate

To a round bottom flask equipped with a stirrer were added 200 ml of acetone, 100 ml of water and 25.3 g of diethyl malonate. To the solution was added 78.9 ml of 2N lithium hydroxide solution, over 5 minutes. After 75 minutes of stirring at ambient temperature, the volatiles were removed, and the residue was suspended in 35 ml of dry dimethylformamide. To it was added 38.3 g of benzyl 6-bromohexanoate and the mixture was stirred at 65° for 20 hours. The mixture was then cooled to ambient temperature, and extracted with 1000 ml of ethyl acetate with brine. The extract was washed twice with brine, and was then concentrated under vacuum. The liquid residue was poured onto silica gel, was washed with 500 ml of heptane, and eluted with 1 liter of 10% ethyl acetate in heptane. Then elution with 1 liter of 15% ethyl acetate in hexane removed the desired product, 22 g of which was obtained by concentration under vacuum. m/e=336.

Preparation 9

Benzyloxycarbonylpentyl ethyl 2-methylenemalonate

A 15 g portion of the product of Preparation 8 was added to a flask equipped with a condenser and stirrer, and 8.4 ml of triethylorthoformate and 8.6 ml of acetic anhydride were added. Then 48 mg of zinc chloride was added, and the mixture was stirred for 16 hours at 125° and then for 3.5 hours at 150°–160°. It was then cooled and extracted into 600 ml of ethyl acetate with brine. The extract was washed twice with brine and concentrated under vacuum. The liquid residue was washed with 500 ml of heptane, with 1500 ml of 15% ethyl acetate in heptane and with 500 ml of 20% ethyl acetate in heptane. Then elution with 500 ml of 40% ethyl acetate in heptane isolated the desired product, in 2.78 g quantity. m/e=392.

Preparation 10

5-Carboxypentyl ethyl 2-methylenemalonate

To a vial equipped with a stirrer was added 0.49 g of 10% palladium on carbon catalyst in 2 ml of absolute ethanol, 1 g of the product of Preparation 9 and 1 ml of 1,4-cyclohexadiene. The vial was capped and stirred for 5 minutes at 60°, and was then cooled to ambient temperature and stirred for 30 minutes more. It was then filtered, and the solution was concentrated under vacuum. The liquid residue was dissolved in a minimal amount of ethyl acetate and was made turbid with heptane, and was then purified by chromatography on silica gel, washing first with 250 ml of 10% ethyl acetate in heptane and then with 250 ml of 30% ethyl acetate in heptane. A 500 ml portion of 50% ethyl acetate in heptane eluted 0.56 g of the desired product, m/e=303.

Preparation 11

Doxorubicin adduct of 5-carboxypentyl ethyl 2-methylene malonate

The intermediate malonate here was bonded to the doxorubicin molecule in the same manner as the product of Preparation 5 above.

The reaction was carried out in the same manner as that of Preparation 5 above, starting with 142 mg of doxorubicin hydrochloride, 159 mg of the product of Preparation 10 and 75.5 mg of sodium bicarbonate. The product was isolated as described in the same preparation, eluting the product from the column with 60 ml of 70% methanol in acetate buffer. That product was further purified as described in Preparation 5 to obtain 95 mg of red solid product, m/e=403, 398.

Preparation 12

Doxorubicin adduct of ethyl N-succinimidoxycarbonylpentyl 2-methylenemalonate

A 12.5 mg portion of the product of Preparation 11 was reacted with 3.6 mg of N-hydroxysuccinimide in the presence of N-methylmorpholine and isobutyl chloroformate, substantially as shown in Preparation 6, to obtain 9.7 mg of the desired product, m/e=896.

EXAMPLE 5

Conjugate of antibody 007B with the doxorubicin adduct of carbonylpentyl ethyl 2-methylenemalonate Two conjugation reactions were carried out. In each case, antibody 007B was supplied as a 0.862 µl portion of solution in 0.34M sodium borate buffer at pH 8.6, containing 17.4 mg/ml of antibody.

1. A 1.17 mg portion of the product of Preparation 12, dissolved in 95.8 µl of dry dimethylformamide, was added.

2. A 1.79 mg portion of the same intermediate was added, dissolved in 95.8 µl of dry dimethylformamide.

Both reactions were stirred at ambient temperature for 1.5 hours, and were then chromatographed on 1.75×25 cm Sephadex G-25M columns. The product-containing fractions in each case were collected, filtered through Millex-GV 0.22 µ filters, and stored at 4° for 16 hours. The products were then filtered again and evaluated by UV spectrophotometry.

1. The recovery was 11.1 mg of conjugate at a concentration of 1.75 mg/ml. The conjugation ratio was 3.8 moles per mole.

2. The recovery was 6.7 mg, at a concentration of 1.33 mg/ml, having a conjugation ratio of 4.5 moles/mole.

Preparation 13

Carboxypentyl ethyl 2-(4-desacetyl-23-desmethoxyvinblastine-23-hydrazo)methylenemalonate A 60.2 mg portion of 4-desacetyl-23-desmethoxyvinblastine-23-hydrazine sulfate was dissolved in 1 ml of dried dimethylformamide, and to it was added 48.6 mg of the product of Preparation 10 dissolved in 0.5 ml of dry dimethylformamide. The mixture was stirred at ambient temperature for 16 hours, and the volatiles were then removed under vacuum. The residue was dissolved in the minimum amount of methanol, and water was added to give a solution in 15% aqueous methanol. The solution was applied to a C18 flash chromatography column, 1.5×6 cm equilibrated with 10% methanol in water. The column was eluted with increasingly concentrated aqueous methanol, and the product was found to elute in fractions containing 60% methanol and 100% methanol. The product-containing fractions were pooled and concentrated under vacuum, and the residue was dissolved in a small amount of methanol. A large amount of benzene was added (100 ml) and the solution was frozen and lyophilized to obtain 46 mg of the desired intermediate, m/e=952.

Preparation 14

Ethyl N-succinimidoxycarbonylpentyl 2-(4-desacetyl-23-desmethoxyvinblastine-23-hydrazo)methylenemalonate A 36.9 mg portion of the product of Preparation 13 was dissolved in 2 ml of dry dimethylformamide and was reacted with 7.56 mg of N-hydroxysuccinimide in the presence of 10.8 µl of N-methylmorpholine and 8.5 µl of isobutyl chloroformate in dry dimethylformamide at −20° for 5 minutes, and the mixture was then warmed gradually to ambient temperature and then heated at 40° for 30 minutes. It was then cooled to ambient temperature and stirred for 16 hours, and the volatiles were removed under vacuum. The residue was dissolved in dichloromethane and applied to a 0.75×6 cm silica gel column. The column was eluted with 20 ml of dichloromethane, and then with 30 ml of 1:1 ethyl acetate:dichloromethane, which eluted out the product. The eluant was concentrated under vacuum to obtain 28.3 mg of the desired product, which was identified by NMR, showing the N-hydroxysuccinimide signal at 2.88 ppm.

EXAMPLE 6

Conjugate of antibody L4KS with carbonylpentyl ethyl 2-(4-desacetyl-23-desmethoxyvinblastine- 23-hydrazo)methylenemalonate Two conjugations were carried out. In each case, antibody L4KS was supplied as 625 μl of solution containing 16 mg/ml in 0.34M sodium borate buffer at pH 0.6.

1. A 0.75 mg portion of the product of Preparation 14, dissolved in 51 μl of dry dimethylformamide, was added to the antibody solution.

2. A 1.2 mg portion of the same intermediate, dissolved in 51 μl of dry dimethylformamide, was added.

Both of the reaction mixtures were stirred at ambient temperature for 1.5 hours and were then centrifuged to separate a white pellet. The supernatants were each chromatographed on 1.75×25 cm Sephadex G-25M columns, equilibrated with physiological phosphate buffered saline and eluted with the same buffer. The product-containing fractions from each column were collected, filtered through Millex-GV 0.22 μ filters, and stored at 4° for 17 days. They were then filtered again in the same manner and evaluated by UV spectrophotometry.

1. The recovery was 6.3 mg of conjugate at a concentration of 1.26 mg/ml, having a conjugation ratio of 2.5 moles/mole.

2. The product was 4.5 mg of conjugate, at a concentration of 0.68 mg/ml, with a conjugation ratio of 3.6 moles/mole.

EXAMPLE 6A

Conjugate of antibody L4KS with carbonylpentyl ethyl 2-(4-desacetyl-23-desmethoxyvinblastine- 23-hydrazo)methylenemalonate The process of Example 6 was repeated, starting with 595 mg of antibody and 57.9 mg of the product of Preparation 14. The product solution was concentrated by vacuum dialysis, and the concentrate was sterile filtered again, to obtain 17.8 ml of solution containing 125 mg of conjugate at a conjugation ratio of 2.8 moles per mole.

EXAMPLE 7

Conjugate of antibody 007B with carbonylpentyl ethyl 2-(4-desacetyl-23-desmethoxyvinblastine- 23-hydrazo)methylenemalonate Three conjugation reactions were carried out. In each case, 10 mg of antibody 007B was supplied as 0.5 ml of solution in 0.34M sodium borate buffer at pH 8.6.

1. A 0.89 mg portion of the intermediate of Preparation 14 was added, in 41 μl of dry dimethylformamide.

2. A 1.20 mg portion of the same intermediate was added in 41 μl of dry dimethylformamide.

3. A 1.49 mg portion of the same intermediate was added in 41 μl of dry dimethylformamide.

All three reactions were stirred at ambient temperature for 1.5 hours, and were then centrifuged and the supernatant was chromatographed as described in Example 6. The product-containing fractions were collected and evaluated by ultraviolet spectrophotometry.

1. The recovery was 5.95 mg of conjugate, at a concentration of 1.35 mg/ml, having a conjugation ratio of 3.0 moles/mole.

2. The recovery was 3.76 mg of conjugate, at a concentration of 0.76 mg/ml, having a conjugation ratio of 3.6 mg/ml.

3. The recovery was 1.54 mg, at a concentration of 0.34 mg/ml, having a conjugation ratio of 6.1 moles/mole.

EXAMPLE 7A Conjugate of antibody 007B with carbonylpentyl ethyl 2-(4-desacetyl-23-desmethoxyvinblastine- 23-hydrazo)methylenemalonate The process of Example 7 was repeated, starting with 396 mg of antibody and 35.6 mg of the product of Preparation 14. The product was vacuum dialyzed and sterile filtered to obtain 39.4 ml of solution containing 307 mg of conjugate at a conjugation ratio of 2.6 moles per mole.

EXAMPLE 8

Conjugate of antibody 9.2.27 with carbonylpentyl ethyl 2-(4-desacetyl-23-desmethoxyvinblastine-23-hydrazo)methylenemalonate Antibody 9.2.27 was taught by Bumol and Reisfeld, *Proc. Natl. Acad. Sci.* (*USA*) 79, 1245 (1982). Three conjugation reactions with that antibody were carried out, starting in each case with 10 mg of antibody in the form of 0.36 ml of solution in 0.34M sodium borate buffer, at pH 8.6.

1. A 0.6 mg portion of the intermediate of Preparation 14, in 41 μl of dry dimethylformamide, was added.

2. A 0.89 mg portion of the same intermediate was added in 41 μl of dry dimethylformamide.

3. A 1.2 mg portion of the same intermediate was added in 41 μl of dry dimethylformamide.

The reaction mixtures were stirred, centrifuged and chromatographed as described above in Example 7 and the products were evaluated by UV spectrophotometry.

1. The recovery was 5.2 mg of conjugate, at a concentration of 0.95 mg/ml, with a conjugation ratio of 3.4 moles/mole.

2. The recovery was 1.5 mg of conjugate at a concentration of 0.32 mg/ml, having a conjugation ratio of 6.1 moles/mole.

3. The recovery was 0.6 mg of conjugate, at a concentration of 0.16 mg/ml, having a conjugation ratio of 7.3 moles/mole.

EXAMPLE 9

Conjugate of antibody L/1C2 with carbonylpentyl ethyl 2-(4-desacetyl-23-desmethoxyvinblastine- 23-hydrazo)methylenemalonate A 2.9 ml portion of solution containing 43 mg of antibody L/1C2 in 0.34M sodium borate buffer at pH 8.6 was combined with 238 μl of solution containing 10.7 mg/ml of the intermediate of Preparation 14 in dry dimethylformamide. The reaction was carried out, and the product was isolated and evaluated, as described in Example 7 above. The recovery was 9.35 of conjugate, at a concentration of 0.69 mg/ml, having a conjugation ratio of 2.6 moles/mole.

Preparation 15

Ethyl N-(2-benzyloxycarbonylethyl)malonamate

To a 100 ml flask were added 2 g of 5% palladium on carbon hydrogenation catalyst, 10 g of benzyl ethyl malonate and 8.6 ml of 1,4-cyclohexadiene. The mixture was stirred at ambient temperature, and the reaction became exothermic after about 40 minutes. Stirring was continued until the reaction mixture had cooled to ambient temperature again, and the mixture was then filtered and the solvent was removed under vacuum from the filtrate. The resulting syrupy residue was dissolved in a minimum amount of ethyl acetate, and was poured through a 150 ml funnel of silica gel. The silica gel was then washed with 400 ml of 20% ethyl acetate in hexane, and then the desired intermediate was eluted with 400 ml of ethyl acetate. The eluent was concentrated under vacuum to obtain 5.48 g of intermediate, as a viscous liquid.

The above intermediate was dissolved in 100 ml of dry dimethylformamide, and 4.77 g of N-hydroxysuccinimide was added and dissolved. Then 8.56 g of dicyclohexylcarbodiimide was added portionwise, and the reaction mixture became exothermic. It was then stirred at ambient temperature overnight, and filtered. A 8.95 g portion of benzyl 3-aminopropionic acid, hydrochloride, was added and dissolved in the filtrate, and then 4.56 ml of N-methylmorpholine was added. The mixture was stirred at ambient temperature for 1½ hours, and the mixture was then extracted into ethyl acetate with brine. The organic layer was then washed with 10% aqueous citric acid, with brine, with saturated aqueous sodium carbonate, and again with brine, and was dried, filtered and concentrated under vacuum. The syrupy residue was dissolved in ethyl acetate, and hexane was added until the solution became cloudy. It was then poured through silica gel, and the silica gel was washed with 200 ml each of 10%, 20% and 30% ethyl acetate in hexane. Then the desired product was eluted with 600 ml of 40% ethyl acetate in hexane. The product solution was concentrated under vacuum to obtain 5.05 g of the desired product, as a pale yellow viscous liquid. It was identified by mass spectroscopy, showing a molecular ion of weight 293. Its elemental analysis was as follows.

Theoretical: C, 61.42; H, 6.57; N, 4.78; Found: C, 61.21; H, 6.31; N, 4.76.

Preparation 16

Ethyl N-(2-benzyloxycarbonylethyl)-2-ethoxymethylenemalonamate

A 5.05 g portion of the product of Preparation 15 was dissolved in 10.7 ml of acetic anhydride and 7.45 ml of triethylorthoformate was added. To the mixture was then added 80 mg of zinc chloride, and the mixture was stirred under reflux, 140°–150°, for 16 hours. It was then cooled to ambient temperature, and the volatiles were removed under vacuum. The residue was extracted with ethyl acetate and brine, and the organic layer was washed with brine, dried, filtered and concentrated under vacuum. The residue was dissolved in a minimum amount of ethyl acetate, and the solution was made cloudy by the addition of hexane. It was then poured through silica gel, and the silica gel was eluted with hexane containing increasing amounts of ethyl acetate. The product-containing fractions, obtained with 30% and 50% ethyl acetate, were collected and concentrated under vacuum to obtain 3.4 g of the desired product, having a molecular ion in mass spectroscopy of weight 349.

Preparation 17

Ethyl N-(2-carboxyethyl)-2-ethoxymethylenemalonamate

A 1.64 g portion of the product of Preparation 16 was added to 10 ml of ethanol and 0.5 g of 5% palladium on carbon hydrogenation catalyst. A 0.89 ml portion of 1,4-cyclohexadiene was added, and the mixture was heated to reflux, cooled and stirred for 1 hour at ambient temperature. It was then reheated, cooled and stirred for an hour more, and then the mixture was filtered and the filtrate was concentrated under vacuum. The residue was triturated with ethyl acetate, and the solids were collected by filtration and washed with diethyl ether to obtain 0.61 g of the desired product, exhibiting mass spectroscopy molecular ions of 260, 244, 214 and 171.

Preparation 18

Ethyl N-(2-carboxyethyl)-2-(4-desacetyl-23-desmethoxyvinblastine-23-hydrazo)methylenemalonamate A 67 mg portion of the product of Preparation 17 was added to a solution of 196 mg of 4-desacetyl-23-desmethoxyvinblastine-23-hydrazine sulfate in 1 ml of dry dimethylformamide. The mixture was stirred at ambient temperature overnight, and the solvent was then removed under vacuum. The residue was dissolved in 20% methanol in 0.5M $KH_2PO_4$ buffer at pH 7, and was applied to a $C_{18}$ reverse phase silica gel column. The column was eluted with the same buffer containing increasing amounts of methanol, and the product-containing fractions were pooled and concentrated under vacuum. The residue was then dissolved in a few ml of water, and the solution was applied to a column of the same type and eluted with water containing increasing amounts of methanol. The product-containing fractions were pooled and concentrated under vacuum to obtain 197 mg of the desired intermediate.

Preparation 19

Ethyl N-(2-succinimidoxycarbonylethyl)-2-(4-desacetyl-23-desmethoxyvinblastine-23-hydrazo)methylenemalonamate A 159 mg portion of the product of Preparation 18 was dissolved in 2 ml of dry dimethylformamide, and to it were added 20.5 mg of N-hydroxysuccinimide, 33.4 mg of dicyclohexylcarbodiimide and 30.8 mg of p-toluenesulfonic acid hydrate. The mixture was stirred at ambient temperature for 24 hours, and the solvent was then removed under vacuum. The residue was taken up in dichloromethane and applied to a silica gel column equilibrated with dichloromethane. The column was eluted with 1:1 isopropanol:dichloromethane, and the product-containing fractions were combined and concentrated under vacuum to obtain 45.2 mg of the desired intermediate.

EXAMPLE 10

Conjugate of antibody 007B with ethyl N-(2-carbonylethyl)2-(4-desacetyl-23-desmethoxyvinblastine-23-hydrazo)methylenemalonamate Three conjugation reactions were carried out, substantially according to the process of Example 6, beginning in each case with 15 mg of antibody in 1.03 ml of borate buffer. The following amounts of the product of Preparation 19 were used in the three reactions.

1. 0.86 mg
2. 1.08 mg
3. 1.30 mg

The three reaction mixtures were stirred at ambient temperature for 1 hour, centrifuged and chromatographed, and the product solutions were sterile filtered to obtain the following products.

|  | 1 | 2 | 3 |
| --- | --- | --- | --- |
| Conjugate | 14.9 mg | 14.9 mg | 13.6 mg |
| Volume | 6.2 ml | 6.5 ml | 7.2 ml |

| | 1 | 2 | 3 |
|---|---|---|---|
| Conjugation Ratio | 3.3 | 4.1 | 4.9 |

EXAMPLE 11

Conjugate of antibody 007B with ethyl N-(2-carbonylethyl)-2-(4-desacetyl-23-desmethoxyvinblastine- 23-hydrazo)methylenemalonamate A conjugation substantially according to Example 6 was carried out, starting with 200 mg of antibody 007B as a 14.6 mg/ml solution and 18 mg of the product of Preparation 19. The product was sterile filtered and vacuum dialyzed to obtain 163 mg of conjugate having a conjugation ratio of 4.3, as a 12.0 mg/μl solution.

Test I

In Vitro Testing

Representative conjugates of the present invention were tested in in vitro systems to demonstrate the activity of the conjugates. In these tests, the potency of conjugates of cytotoxic drugs was determined by measuring the cytotoxicity of the conjugates against tissue cultures of cells of human cancer origin. The cells used were the UCLA/P3 cell line, a human lung adenocarcinoma, and the T222 cell line, a human squamous carcinoma. The following table reports the activity of the conjugates as the 50% inhibitory concentration, based on the amount of drug in the conjugate.

| Example | UCLA/P3 | T222 |
|---|---|---|
| 2A | 0.1 μg/ml | >10 μg/ml |
| 2B | >10 | >10 |
| 3A | >10 | >10 |
| 4 | >10 | |
| 4A | >10 | 3.3 |
| 6A | <0.0001 | |
| 11 | 0.26 | |

Test II

UCLA/P3 in Mice

The conjugate of Example 6A was tested in vivo against xenografts of the UCLA/P3 lung adenocarcinoma in female Charles River nude mice. The test was begun by implanting each mouse subcutaneously with $10^7$ UCLA/P3 tumor cells. On each of days 2, 5 and 8 after implantation, each mouse was injected with the conjugate, or with physiological buffered saline as an untreated control. The doses of conjugate ranged from 0.09 mg/kg up to 3 mg/kg, based on the amount of drug. The size of the tumors induced by implantation was measured on days 15, 21 and 28 after implantation. Each treatment group consisted of five mice, except for the untreated control group, which consisted of 10 mice.

At 28 days, 100% suppression of the tumors was produced by all treatments of 0.38 mg/kg or more. The 0.19 mg/kg treatment gave about 60% suppression, and the 0.09 mg/kg treatment gave about 25% of suppression of tumor growth.

Test III

UCLA/P3 Tumors in Mice

The conjugate of Example 7A was tested against tumors induced by implantation of UCLA/P3 cells in mice, substantially as described in Test II. In this case, conjugate was administered at doses of 0.25, 0.5, 1 and 2 mg/kg, based on the amount of drug, and doses were administered on days 16, 19, 22 and 25 after implantation. The tumors were measured on the same days.

It was found that the 0.25 mg/kg dose gave slight control of the tumors, and that, by 50 days after implantation, the mice on that dose had massive tumors averaging about 7500 mg. The control mice had tumors averaging about 8000 mg at that time. The other doses, however, gave substantial suppression of the tumors.

At 70 days after implantation, the mice which received 0.5 mg/kg had tumors averaging about 4000 mg; the mice receiving 1 mg/kg had tumors averaging about 2000 mg; and the mice receiving 2 mg/kg had tumors averaging only about 500 mg.

Compositions and Methods of Use

The conjugates of the present invention are useful in the treatment methods which are important parts of the present invention. Accordingly, the invention also includes pharmaceutical compositions for parenteral administration which are used in the treatment methods. Such compositions are formulated by methods commonly used in pharmaceutical chemistry. The present conjugates are acceptably soluble in physiologically-acceptable fluids, such as physiological saline solutions and other aqueous solutions which can safely be administered parenterally.

Products for parenteral administration are often formulated and distributed in solid, preferably freeze dried form, for reconstitution immediately before use. Such formulations are useful compositions of the present invention. Their preparation is well understood by pharmaceutical chemists; in general, they comprise mixtures of inorganic salts, to confer isotonicity, and dispersing agents such as lactose, to allow the dried preparation to dissolve quickly upon reconstitution. Such formulations are reconstituted for use with highly purified water to a known concentration.

The conjugates and compositions comprising the conjugates are used for treatment of patients who are in need of treatment with the drug comprised by the conjugate. The specific purpose of the treatment, and the dose range to be administered, depends on the identity of the drugs and the condition for which the patient is to be treated. Guidance as to the specific potencies of drug and their appropriate dosage ranges is to be obtained from the standard medical literature.

I claim:

1. A derivatized drug of the formula

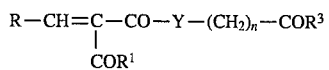

wherein

R is a drug having a reactively-available amino, hydroxy, or thiol function;

$R^1$ is a carboxylic acid protecting group;

Y is —O—, —NH—, —NCH$_3$—, or —NC$_2$H$_5$—;

n is an integer from 1 to about 8;

$R^3$ is hydroxy, a carboxylic acid protecting group, a carboxylic acid activating group selected from the group consisting of benzenesulfonyloxy, methanesulfonyloxy, toluenesulfonyloxy, phthalimidyloxy, succinimidyloxy, chloro, benzotriazolyloxy, bromo, and azido or a moiety which completes a salt of the carboxylic acid;

said carboxylic acid protecting groups being independently selected from the group consisting of methoxymethoxy, tetrahydropyranyloxy, tetrahydrofuranyloxy, benzyloxymethoxy, phenacyloxy, substituted phenacyloxy, 2,2,2-trichloroethoxy, haloethoxy, trimethylsilylethoxy, methylthioethoxy, toluenesulfonylethoxy, t-butoxy, cyclopentoxy, benzyloxy, diphenylmethoxy, triphenylmethoxy, amino, ethylamino, dimethylamino, pyrrolidino, morpholino, piperidino, diethylaminoethylamino, morpholinoethylamino, and benzylmethylaminoethylamino 2. A derivatized drug of claim 1 wherein R is a drug having a reactively-available amino function.

3. A derivatized drug of claim 1 wherein R is a drug having a reactively-available hydroxy function.

4. A derivatized drug of claim 1 wherein R is a drug having a reactively-available thiol function.

* * * * *